United States Patent [19]

Adams et al.

[11] Patent Number: 5,080,871

[45] Date of Patent: Jan. 14, 1992

[54] APPARATUS FOR ALKYLATION OF ORGANIC AROMATIC COMPOUNDS

[75] Inventors: John R. Adams, Houston; Lawrence A. Smith, Jr., Bellaire, both of Tex.

[73] Assignee: Chemical Research & Licensing Company, Houston, Tex.

[21] Appl. No.: 620,628

[22] Filed: Dec. 3, 1990

Related U.S. Application Data

[62] Division of Ser. No. 321,359, Mar. 10, 1989, Pat. No. 5,019,669.

[51] Int. Cl.$^5$ ............................................. B01J 8/04
[52] U.S. Cl. .................... 422/187; 203/DIG. 6; 422/189; 422/191; 422/234
[58] Field of Search ............ 585/446, 400.451, 457, 585/467; 203/DIG. 6; 422/187, 189, 190, 191, 234, 235

[56] References Cited

U.S. PATENT DOCUMENTS

| | | | |
|---|---|---|---|
| 2,676,876 | 4/1957 | Barr | 422/191 |
| 3,629,478 | 12/1971 | Haunschild | 203/DIG. 6 |
| 3,634,539 | 1/1972 | Haunschild | 203/DIG. 6 |
| 4,215,011 | 7/1980 | Smith | 252/426 |
| 4,232,177 | 11/1980 | Smith | 585/324 |
| 4,242,530 | 12/1980 | Smith | 585/510 |
| 4,250,052 | 2/1981 | Smith | 252/426 |
| 4,302,356 | 11/1981 | Smith | 252/426 |
| 4,307,254 | 12/1981 | Smith | 568/698 |
| 4,316,997 | 2/1982 | Vaughan | 385/458 |
| 4,371,714 | 2/1983 | Young | 568/628 |
| 4,423,254 | 12/1983 | Olah | 568/781 |
| 4,443,559 | 4/1984 | Smith | 502/527 |
| 4,469,908 | 9/1984 | Burress | 585/467 |
| 4,482,775 | 11/1984 | Smith | 203/DIG. 6 |
| 4,519,875 | 5/1985 | Becker | 203/28 |
| 4,540,831 | 9/1985 | Briggs | 568/697 |
| 4,556,750 | 12/1985 | Cobb | 585/446 |
| 4,849,569 | 7/1989 | Smith | 585/446 |
| 4,898,716 | 2/1990 | Hsia et al. | 203/DIG. 6 |
| 4,950,834 | 8/1990 | Arganbright et al. | 585/446 |
| 4,973,453 | 11/1990 | Agee | 422/190 |
| 4,973,780 | 11/1990 | Johnson et al. | 585/446 |

Primary Examiner—Peter Kratz
Attorney, Agent, or Firm—Kenneth H. Johnson

[57] ABSTRACT

Organic aromatic compounds are alkylated in a Reactive Distillation ™ reactor, wherein the solid particulate catalyst is slurried in the aromatic feed stream and fed to a reaction zone containing inert distillation packing. Olefin is vaporized and fed to the bottom of the reaction zone and agitates the catalyst while reacting the olefin with the aromatic to form an alkylation product. The alkylation product is removed from the lower end of the reaction zone and recovered. Any unreacted aromatic is distilled overhead and recycled or recovered. Recycling the aromatic controls the molar ratio of aromatic to olefin to the extent that substantially all of the olefin is reacted.

6 Claims, 1 Drawing Sheet

APPARATUS FOR ALKYLATION OF ORGANIC AROMATIC COMPOUNDS

This is a division of application Ser. No. 07/321,359, filed Mar. 10, 1989, now U.S. Pat. No. 5,019,669.

BACKGROUND OF THE INVENTION

1. Field of the Invention

The present invention relates to a process for the alkylation of organic aromatic compounds. More particularly the invention relates to a process for the concurrent alkylation and distillation of reaction components (reactants and products) in a catalyst bed wherein the catalyst is slurried in the organic aromatic compound and passed through a reaction distillation zone to contact olefin feed. The reaction distillation zone comprises inert distillation packing contained within the lower portion of a distillation column reactor.

2. Related Art

Ethyl benzene and cumene are currently produced by the reaction of benzene and the respective olefin, i.e., ethylene and propylene by acid catalysis. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large volume recycle in conventional processes.

U.S. Pat. Nos. 4,371,714 and 4,469,908 disclose straight pass alkylation of aromatic compounds using molecular sieve catalysts in fixed beds, however, both references disclose coking of the catalyst as a problem which necessitates frequent unit shut down and regeneration of the catalyst. U.S. Pat. Nos. 4,316,997 and 4,423,254 both disclose the use of acidic resins in fixed beds for the alkylation of aromatic compounds. Coking is also a problem with these catalysts.

Recently a new method of carrying out catalytic reactions has been developed, wherein the components of the reaction system are concurrently separable by distillation, using the catalyst structures as the distillation structures. Such systems are described variously in U.S. Pat. Nos. 4,215,011; 4,232,177; 4,242,530; 4,250,052; 4,302,356; 4,307,254; and 4,443,559 commonly assigned herewith. Briefly, a structure described there is a cloth belt with a plurality of pockets spaced along the belt, which is then wound in a helix about a spacing material such as stainless steel knitted mesh. These units are then disposed in the distillation column reactor.

In commonly owned, copending U.S. patent application Ser. No. 122,485 filed 11/15/87, the process of alkylating aromatic compounds with olefins was carried out in a catalytic distillation system using a catalyst structure as described above, using either molecular sieves or acidic resins as particle packing in the pockets. This process has a far greater resistance to coking than the straight pass systems.

The present system differs from catalytic distillation, because the catalyst bed is not fixed and does not serve as the distillation structure in the system. Hence the present system is designated as Reactive Distillation ™.

Advantages of the present invention are that the catalysts are not highly corrosive and do not require periodic cyclic regeneration, the heat of reaction is used efficiently, only low volume of recycle is required and the feed ratios can approach unity.

SUMMARY OF THE INVENTION

Briefly, the present invention is a process for the alkylation of organic aromatic compounds by contacting the organic aromatic compound and a $C_2$ to $C_{20}$ olefin in a distillation column reactor containing a moving bed of acidic catalyst slurried in the organic aromatic compound fee in a distillation reaction zone containing an inert distillation packing thereby catalytically reacting said organic aromatic compound and said olefin to produce an alkylated organic aromatic product and concurrently in said moving bed fractionating the resultant alkylated organic product from the unreacted materials. The downwardly flowing catalyst slurry provides the catalytic sites while the inert packing provides the distillation sites. The alkylated organic aromatic product along with a portion of the unreacted organic aromatic compound containing the slurried catalyst is withdrawn from the distillation column reactor at a point below the fixed bed and additional unreacted organic aromatic compound and unreacted olefin may be taken off as an overhead. The catalyst is separated from the bulk of the liquid and a portion carried back to the reaction zone as a slurry. Another portion of the recovered catalyst is withdrawn and sent to a separate regeneration. Regenerated catalyst may be returned to the reactor with the organic aromatic feed. Make up catalyst may also be added to the aromatic feed or the catalyst recycle. The combine alkylation product and unreacted organic aromatic compound is separated in a fractional distillation column, with the organic aromatic being recycled back to the reaction zone.

Suitable acidic catalysts include molecular sieves (mole sieves) and cation exchange resins. More specifically the mole sieve or cation exchange resin catalyst is of such a nature as to allow vapor flow through the bed to agitate and distribute the catalyst within the inert packing, yet provide a sufficient surface area for catalytic contact as described in the previously noted U.S. Pat. Nos. 4,215,011, 4,302,356 and 4,443,559 which are incorporated herein in their entirety.

BRIEF DESCRIPTION OF THE DRAWING

The drawing is a schematic representation of a preferred embodiment of one species of the present invention for producing ethyl benzene.

DETAILED DESCRIPTION OF THE INVENTION

Figure 1:
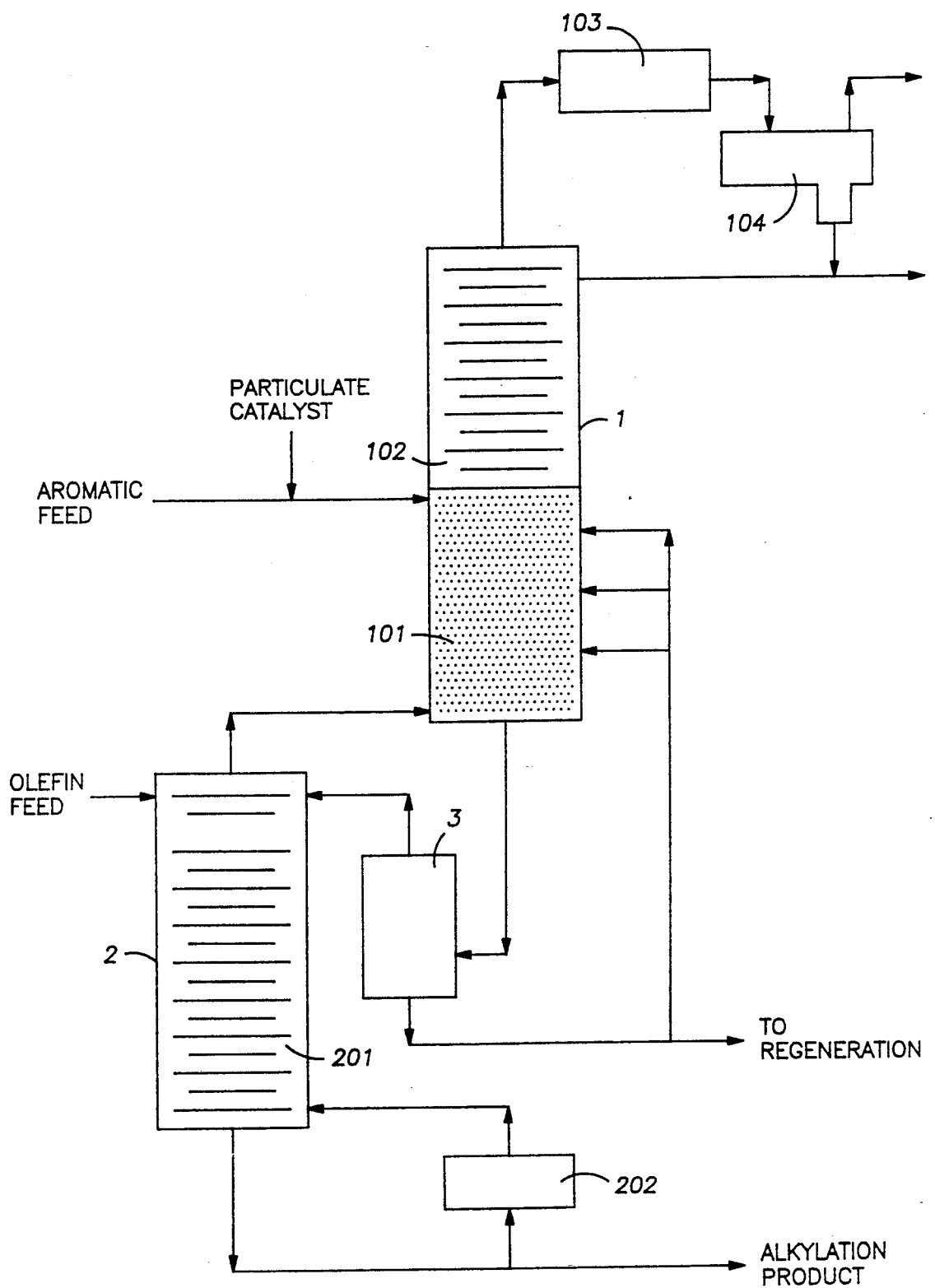

The exact location of the olefin feed will depend on the particular feeds and the desired product. In one embodiment the olefin feed in vapor phase to the reaction is preferably made below the catalyst bed thereby allowing mixing of reactants and agitation of the catalyst bed. In another embodiment the olefin feed to the reaction is preferably made into upper end of the fractionation column used to separate the unreacted organic aromatic compound form the alkylation product thereby allowing vaporization of this reactant along with the organic aromatic compound and insuring good mixing to thereby react as much of the two as possible and reduce or eliminate the olefin leaving the reactor as overhead. A combination of olefin feed points may be employed.

The organic aromatic compound feed may be added at any point in the reactor, however, preferably it is added at the top of the distillation reaction zone. In any event a portion of the aromatic feed, sufficient to slurry the catalysts particles will be fed at the point where it is desired to have the catalyst present in the reactor. The entire section of distillation structure need not have catalyst in it, in fact it is contemplated that a substantial portion of the distillation reactor will contain conventional distillation structures, such as, trays or plates absent any added catalyst (other than incidental particles of catalyst carried up into that section by the boil up in the column. Also, in order to achieve high selectivity toward monosubstitution (which is a preferred aspect of the present invention), there is a large excess of the organic aromatic compound to the olefin in the reactor in the range of 2 to 100 moles of organic aromatic compounds per mole of olefin, that is the net molar feed ratio of aromatic organic compound olefin may be close to 1:1, although the system is operated so as to maintain a substantial molar excess of organic aromatic compound to olefin in the reaction zone. The alkylated product is the highest boiling material and is separated in the lower portion of the column usually as bottoms. The organic aromatic compound can be the second highest boiling or third highest boiling component (excluding inerts) as noted above, however, by operating with a large excess of the organic aromatic compound, the major portion of the olefin is reacted; thereby reducing the separation and recovery problems. The operation of Reactive Distillation ™ lies in an understanding of the principles associated with distillation. First, because the reaction is occurring concurrently with distillation, the initial reaction product is removed from the reaction zone as quickly as it is formed. The removal of the alkylation product minimizes polysubstitution, decomposition of the alkylation product and/or oligomerization of the olefin. Second, because the organic aromatic compound is boiling, the temperature of the reaction is controlled by the boiling point of that component at the system pressure. The heat of the reaction simply creates more boil up, but no increase in temperature. Third, the reaction has an increased driving force because the reaction products have been removed and cannot contribute to a reverse reaction (Le Chatelier's Principle).

As a result, a great deal of control over the rate of reaction and distribution of products can be achieved by regulating the system pressure. Also, adjusting the through-put (residence time a liquid hourly space velocity) gives further control of product distribution and degree of olefin conversion.

The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the reactant/product composition in the column. To change the temperature the pressure is changed. Temperature control in the reaction zone is thus controlled by the pressure; by increasing the pressure, the temperature in the system is increased, and vice versa. It can also be appreciated that in Reactive Distillation ™ as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

The olefins may be $C_2$ to $C_{20}$ olefins, preferably $C_2$ to $C_{12}$ olefins, including normal and branched forms thereof. For example, suitable olefins are ethylene, propylene, butylene, isobutylene, 1-pentene, 1-hexene, 2-hexene, 2,3-dimethyl-1-pentene, 1-octene, diisobutylene, 1-nonene and 1-decene, dodecene and the like. The olefins may contain substituents which do not interfere with the alkylation. In one preferred embodiment the olefin is a $C_2$ to $C_4$ olefin.

In some reactions according to the present invention, the olefin will be a higher boiling material than the organic aromatic compound, e.g., $C_8$ to $C_{20}$ olefins. In such instances any unreacted olefin will appear in the bottoms alkylation product, although a side draw may be used to reduce such material in the product to an insignificant level. However, operating the reaction with far less than a stoichiometric amount of olefin in the reaction zone, as described, will normally keep the olefin level in the bottoms low or entirely eliminated.

In those instances wherein the olefin is lower boiling than the organic aromatic compound, e.g., $C_2$ to $C_7$ compound there may be some olefin going overhead even with the large molar excess present in the reaction zone. In those instances the overhead may be condensed to remove a major portion of the organic aromatic compound and the olefin and inerts removed for further separation or use. Similarly inerts such as the alkane of the particular olefin(s) which are often found in olefin streams will be a possible contaminant, depending on its boiling point, in either the bottoms or overhead.

The organic aromatic compounds are preferably those having a boiling point of 250° C. or less under the pressure conditions of the distillation column reactor. The organic aromatic compounds include hydrocarbons of one or more rings and 6 to 20 carbon atoms which may contain substituents which do not interfere with the alkylation including halogen (Cl, Br, F and I), OH and alkyl, cycloalkyl, aralkyl and alkaryl radicals of 1 to 10 carbon atoms. Suitable organic aromatic compounds include benzene, xylene, toluene, phenol, cresol, ethyl benzene, diethyl benzene, naphthalene, indene, phenyl bromide, 1-bromo-2-chloro-benzene, 1-bromo-4-cyclohexyl benzene, 2-bromo-1,4-dihydroxy-benzene, 1(bromo-methyl) naphthalene, 1,2-dihydronaphthalene and the like, a preferred group of compounds for use in the present process is benzene, xylene, toluene, phenol, and cresol.

The mole ratio of organic aromatic compound to olefin in the reaction zone may be in the range of 2 to 100:1, preferably 2 to 50:1 and more desirably about 2 to 10:1. The greater the excess of organic aromatic compound the more the selectivity to the monosubstituted product is improved. Alkylation is forced to completion, since the simultaneous and concurrent fractionation and removal of the alkylation product from the distillation column reactor does not allow the products to contribute to the reverse reaction (Le Chatelier's Principle). However, very large molar excesses of organic aromatic compounds require a very high reflux ratio, and a low unit productivity. Hence, the correct ratio of organic aromatic compound to olefin must be determined for each combination of reactants as well as the acceptable olefin content in either the overhead or alkylation product (as described above), in a particular embodiment which is of current commercial importance ethylene or propylene is reacted with benzene according to the present invention to form ethyl benzene or cumene, respectively. In both of these reactions the olefin is the most volatile component and it is desirable to react it rather than have some carried off overhead.

The length of the catalyst bed (that portion of the distillation reactor where the down flowing catalyst slurry is present), particularly that portion wherein the reactants are in contact and the major portion of the reaction occurs, depends on the reactants, location of the olefin feed and the acceptable unreacted olefin in the streams leaving the tower. Some degree of development testing will be required for each set of reactants and parameters of stream purity following present disclosures.

The present alkylation reaction can be carried out at sub-through super atmospheric pressure, e.g., 0.20 to 40 atmospheres. The temperature will vary depending on the reactants and product. Furthermore, the temperature along the column will be as in any distillation column, the highest temperature will be in the bottom and the temperature along the column will be the boiling point of the compositions at that point in the column under the particular conditions of pressure. Moreover, the exothermic heat of reaction does not change the temperature in the column, but merely causes more boil up. However, the temperatures within the column with the above considerations in mind will generally be in the range of 50° C. to 500 C., preferably 70° C. to 500° C. for the mole sieve and 70° C. to 200° C. for the cation exchange resin, and more preferably in the range of about 80° C. to 300° C. at pressures of 0.5 to 20 atmospheres for the mole sieve, and about 80° C. to 150° C. at 0.25 to 15 atmospheres for the resin catalyst.

Molecular sieves are porous crystalline, three-dimensional alumina-silicates of the zeolite mineral group. The crystal skeleton is composed of silicon and aluminum atoms each surrounded by four oxygen atoms to form. The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e. in so far as the natural zeolites are the functional equivalents to the synthetic zeolites.

Usually synthetic zeolites are prepared in the sodium form, that is, with a sodium cation in close proximity to each aluminum tetrahedron and balancing its charge. To date seven principal types of molecular sieves have been reported, A, X, Y, L, erionite, omega and mordenite. The A type have relative small pore size. By the term pore size is meant the effective pore size (diameter) rather than the free pore size (diameter). Types X and Y have larger pore size (approximately 10 Å) and differ as to the range of ratio of $Al_2O_3$ to $SiO_2$ as:

Type X--------------- $Al_2O_3$/2.0–3.0 $SiO_2$

Type Y--------------- $Al_2O_3$/3.0–6.0 $SiO_2$

Type L and the other types listed have still higher ratios of $SiO_2$ to $Al_2O_3$ The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with ammonium hydroxide to remove the Na and thereafter the mole sieve is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability. In addition to mole sieves which are acidic according to the Bronsted Theory those mole sieves which exhibit acidic characteristics under the Lewis Theory, for example, calcium exchanged mole sieves are suitable for the present reaction. By exchanging the univalent cations (e.g.) $Na^+$) with multivalent cation, strong ionic activity is imparted. The ratio of $SiO_2$: $Al_2O_3$, valence and radius of the cation and the extent of exchange all affect the catalyst activity. In general activity increases with (1) increased $SiO_2$ $Al_2O_3$ ratio, (2) decreased cation radius and an increase in cation valence. The effect of replacing univalent ions (e.g. $Na^{30}$) with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention.

It would appear that the pore size within the crystal lattice may affect the selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal.

The acid form mole sieves are generally produced and available as particles in the range of <10 micron (powders) to 0.2 inch in diameter (beads).

In this form the mole sieves form too compact a bed and will not function adequately in a distillation, since there is a very large pressure drop through the bed and the free flow of internal reflux and rising vapor is impeded. However, when slurried with the aromatic and fed to a fixed bed of inert distillation packing and further agitated by a vapor (e.g., olefin) rising through the bed, they present only an incremental increase in the hydrostatic resistance in the tower to the flow of the vapors, than the carrier liquid (e.g., aromatic feed) alone.

Suitable acid cation exchange resins include those which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethyl benzene, methyl styrene, vinyl ohlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymer which already contain sulfonic acid groups; for example, by treatment with fuming sulfuric acid, i.e., sulfuric acid which contains sulfur trioxide. The treatment with fuming sulfuric acid is preferably carried out at 0° to 150° C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification 908,240). The ion exchange resin is generally used in a granular size of about 0.25 to 1 mm, although particles from 0.15 mm up to about 2 mm may be employed. The finer catalysts provide high surface area, but could also result in high pressure drops through the reactor requiring higher vapor velocities to agitate the catalyst. The macroreticular form of these catalysts have much larger surface area exposed and limited swelling which all of these resins undergo in a non-aqueous hydrocarbon medium compared to the gelular catalysts.

The concentration of catalyst in the slurry can vary over a wide range, depending on such process variables as the catalyst particle size, particle density, surface area, olefin feed rate, ratio of aromatic to olefin, temperature and catalyst activity. As an illustration, a Y type mole sieve, 80–20 mesh particle size, 770 m$^2$/gm. surface area, in the reaction of ethylene with benzene with benzene being fed at 78 g/min, ethylene at 28 g/min, benzene reflux ratio of 4:1, the concentration of catalyst in the benzene feed plus recycle could be in the range of 50 to 100 grams per liter. The competing considerations of reactivity and physical dynamics of the reactants in a particular system may necessitate adjustment of several variables to approach a desired result.

The drawing illustrates one species of the present invention, i.e., the production of ethyl benzene by alkylating benzene with ethylene and a preferred embodiment of that species. Referring to the drawing the distillation column reactor is divided into two sections. The upper section 1, which may be a separate column is either completely filled with inert distillation packing or at least has the lower one-third to one-half filled with such packing as at 101. The upper two-thirds to one-half of the first section 1 may alternatively have conventional distillation trays 102. The lower portion 101 of the first section is considered the reaction zone for reasons which will become apparent. The second section 2, below the first may conveniently be a second conventional distillation column having conventional trays 201.

The particulate catalyst as described is slurried into the organic aromatic feed and the two combined are fed to the top of the reaction zone 101. The olefin is vaporized, as in the upper end of the second section 2 as shown, and fed to the lower end of the reaction zone 101. The vaporous olefin rises in the reaction zone agitating the slurried catalyst and insuring good contact. As the olefin rises through the slurry bed it is in contact with the organic aromatic and catalyst thus reacting the two to form an alkylation product. In the embodiment shown, ethylene or propylene (propylene) reacts with benzene to form ethyl benzene or cumene. A molar excess of benzene to olefin is maintained in the reaction zone such that essentially all of the olefin is consumed. Unreacted benzene is boiled out of the catalyst mixture up into the conventional distillation trays 102 where any alkylation product is separated back down to the distillation reaction section and out the bottom of the reaction zone 101. The slurried catalyst along with some of the unreacted benzene is also carried out the bottom since separation is not complete. The bulk of the liquid (unreacted benzene and alkylation product) is separated from the catalyst in a separator 3 and fed to the top of the second section 2 where separation is completed. The catalyst, still slurried in some of the liquid is returned to the reaction zone. Some of the catalyst may be removed in a slip stream for regeneration and reslurrying with benzene feed.

In the second section the separation of benzene and alkylation product is complete with benzene being returned to the reaction zone. As noted above, the olefin may be fed to the top of the second section 2 to be vaporized prior to introduction to the reaction zone 101. Alkylation product is withdrawn from the bottom of second section 2 where some is heated in reboiler 202 to provide heat for the distillation.

Benzene is taken overhead the first section 1 where it may be condensed in condenser 103 and collected in receiver/separator 104. Substantially all of the benzene is returned to the distillation column reactor section 1 as reflux and to aid in the control of the molar ratio of benzene to olefin in the reaction zone. Any unreacted or inert gases are removed in the separator/receiver 104 for further processing as desired. The recycle of slurried catalyst in benzene-alkylation product from the bottom of the reaction zone may also be used to control the molar ratio.

The invention claimed is:
1. An apparatus for conducting concurrent and simultaneous reaction and distillation comprising:
   (a) a first distillation column having:
      (i) an upper portion defining a first distillation zone containing distillation structures,

(ii) a lower portion defining a reaction zone containing distillation structures comprising inert distillation packing, (iii) first inlet means to add a slurry of particulate catalyst and at least one liquid organic reactant to said first distillation column, (iv) liquid slurry outlet means at the bottom of said first distillation column, and (v) first vapor outlet means at the top of said first distillation column, (b) a catalyst separator operably connected by a first conduit to said liquid slurry outlet means for receiving a slurry of said catalyst and a liquid containing a reaction product and separating said catalyst from said liquid containing a reaction product;

(c) catalyst outlet means to remove separated particulate catalyst from said separator;

(d) first liquid outlet means connected to said catalyst separator to remove said separated liquid containing a reaction product from said separator; and (e) a second distillation column having
  (i) second inlet means near the upper end connected by a second conduit to said first liquid outlet means,
  (ii) second vapor outlet means at the top, and
  (iii) second liquid outlet means at the bottom, and
  (iv) a third inlet means to add a second organic reactant to the upper end of said second distillation column.

2. The apparatus of claim 1 further comprising:
condensing means operably connected by a third conduit to said first vapor outlet means; and
liquid reflux means comprising a fourth, conduit operably connecting said condensing means to the upper portion of said first distillation column.

3. The apparatus of claim 1 further comprising a fifth conduit connecting said catalysts outlet means of said catalyst separator to said first distillation column to return said removed particulate catalyst to said first distillation column.

4. The apparatus of claim 3 further comprising a sixth conduit connected to said catalyst outlet means of said catalyst separator to withdraw a portion of said removed particulate catalyst for regeneration.

5. An apparatus for conducting concurrent and simultaneous reaction and distillation comprising:
(a) a first distillation column having:
  (i) an upper portion defining a first distillation zone containing distillation structures,
  (ii) a lower portion defining a reaction zone containing distillation structures comprising inert distillation packing,
  (iii) first inlet means to add a slurry of particulate catalyst and at least one liquid organic reactant to said first distillation column,
  (iv) liquid slurry outlet means at the bottom of said first distillation column, and
  (v) first vapor outlet means at the top of said first distillation column,
(b) a catalyst separator for receiving a slurry of said catalyst and a liquid containing a reaction product to separate said catalyst from said liquid,
  (i) connected to said liquid slurry outlet means of said first distillation column
  (ii) and having a first liquid outlet means;
(c) a second distillation column having
  (i) second inlet means near the upper end connected by a second conduit to said first liquid outlet means,
  (ii) second vapor outlet means at the top, and
  (iii) second liquid outlet means at the bottom, and
  (iv) a third inlet means to add a second organic reactant to the upper end of said second distillation column;
(d) condensing means operably connected to said first vapor outlet means by a third conduit;
(e) liquid reflux means comprising a fourth conduit operably connecting said condensing means to the upper portion of said first distillation column;
(f) a fifth conduit connecting said catalyst outlet means of said catalyst separator to said first distillation column to return said removed particulate catalyst to said first distillation column; and
(g) a sixth conduit connected to said catalyst outlet to withdraw a portion of said removed particulate catalyst for regeneration.

6. The apparatus of claim 5 further comprising a seventh conduit connecting said second vapor outlet means of said second distillation column to the lower end of said first distillation column.

* * * * *